US00PP25133P2

(12) United States Plant Patent
Goldup

(10) Patent No.: US PP25,133 P2
(45) Date of Patent: Dec. 2, 2014

(54) ***ACACIA* PLANT NAMED 'ACCOG01'**

(50) Latin Name: *Acacia cognata*
Varietal Denomination: ACCOG01

(71) Applicant: Peter Goldup, Mt. Evelyn (AU)

(72) Inventor: Peter Goldup, Mt. Evelyn (AU)

( * ) Notice: Subject to any disclaimer, the term of this patent is extended or adjusted under 35 U.S.C. 154(b) by 53 days.

(21) Appl. No.: 13/815,333

(22) Filed: Feb. 21, 2013

(51) Int. Cl.
*A01H 5/00* (2006.01)

(52) U.S. Cl.
USPC ..... Plt./226

(58) Field of Classification Search
CPC ..... A01H 5/02; A01H 1/00; A01H 1/02; A01H 1/04; A01H 3/00; A01H 3/04; A01H 4/005
USPC ..... Plt./226
See application file for complete search history.

*Primary Examiner* — Annette Para
(74) *Attorney, Agent, or Firm* — C. A. Whealy

(57) ABSTRACT

A new and distinct cultivar of *Acacia* plant named 'ACCOG01', characterized by its compact, semi-upright to outwardly arching and rounded plant habit; moderately vigorous growth habit; freely branching habit; dense and bushy appearance; and numerous dark green-colored phyllodes that are broad and medium in length.

1 Drawing Sheet

Botanical designation: *Acacia cognata.*
Cultivar denomination: 'ACCOG01'.

BACKGROUND OF THE INVENTION

The present invention relates to a new and distinct cultivar of *Acacia* plant, botanically known as *Acacia cognata* and hereinafter referred to by the name 'ACCOG01'.

The new *Acacia* plant is a product of a planned breeding program conducted by the Inventor in Mt. Evelyn, Victoria, Australia. The objective of the breeding program is to create new compact *Acacia* plants with attractive growth habit and foliage.

The new *Acacia* plant originated from an open-pollination in Mt. Evelyn, Victoria, Australia in 2000 of an unnamed selection of *Acacia cognata*, not patented, as the female, or seed parent with an unknown selection of *Acacia cognata* as the male, or pollen, parent. The new *Acacia* plant was discovered and selected by the Inventor as a single plant from within the progeny of the stated open-pollination in a controlled greenhouse environment in Mt. Evelyn, Victoria, Australia in 2001.

Asexual reproduction of the new *Acacia* plant by cuttings in Mt. Evelyn, Victoria, Australia since 2001 has shown that the unique features of this new *Acacia* plant are stable and reproduced true to type in successive generations.

SUMMARY OF THE INVENTION

Plants of the new *Acacia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'ACCOG01'. These characteristics in combination distinguish 'ACCOG01' as a new and distinct *Acacia* plant:

1. Compact, semi-upright to outwardly arching and rounded plant habit.
2. Moderately vigorous growth habit.
3 Freely branching habit; dense and bushy appearance.
4. Numerous dark green-colored phyllodes that are broad and medium in length.

Plants of the new *Acacia* can be compared to plants of the female parent selection. Plants of the new *Acacia* differ primarily from plants of the female parent selection in the following characteristics:

1. Plants of the new *Acacia* are more compact than plants of the female parent selection.
2. Plants of the new *Acacia* are denser than plants of the female parent selection.

Plants of the new *Acacia* can be compared to plants of *Acacia cognata* 'Limelight', not patented. In side-by-side comparisons conducted in Mt. Evelyn, Victoria, Australia, plants of the new *Acacia* differed primarily from plants of 'Limelight' in the following characteristics:

1. Plants of the new *Acacia* were more outwardly arching than and not as upright as plants of 'Limelight'.
2. Plants of the new *Acacia* were shorter and broader than plants of 'Limelight'.
3. Phyllodes of plants of the new *Acacia* were shorter and broader than phyllodes of plants of 'Limelight'.
4. Phyllodes of plants of the new *Acacia* were darker green in color than phyllodes of plants of 'Limelight'.

BRIEF DESCRIPTION OF THE PHOTOGRAPH

The accompanying colored photograph illustrates the overall appearance of the new *Acacia* plant showing the colors as true as it is reasonably possible to obtain in colored reproductions of this type. Colors in the photograph may differ slightly from the color values cited in the following detailed botanical description which accurately describe the actual colors of the new *Acacia* plant. The photograph comprises a side perspective view of a typical plant of 'ACCOG01' grown in a container.

DETAILED BOTANICAL DESCRIPTION

The aforementioned photograph and following observations, measurements and values describe plants grown in 20-cm containers during the summer and early winter in a polyethylene-covered greenhouse in Cranbourne, Victoria, Australia and under cultural practices typical of commercial *Acacia* production. During the production of the plants, day temperatures ranged from 10° C. to 40° C., night temperatures ranged from 4° C. to 25° C. and light levels ranged from 5,000 to 9,000 foot-candles. Plants were one year old when the photograph and description were taken. In the following description, color references are made to The Royal Horticultural Society Colour Chart, 2007 Edition, except where general terms of ordinary dictionary significance are used.

Botanical classification: *Acacia cognata* 'ACCOG01'.

Parentage:

*Female, or seed, parent*.—Unnamed selection of *Acacia cognata*, not patented.

*Male, or pollen, parent*.—Unknown selection of *Acacia cognata*, not patented.

Propagation:

*Type*.—By cuttings.

*Time to initiate roots, summer*.—About 35 days at 22° C.

*Time to initiate roots, winter*.—About 55 days at 22° C.

*Time to produce a rooted young plant, summer*.—About 84 days at 22° C.

*Time to produce a rooted young plant, winter*.—About 100 days at 14° C.

*Root description*.—Fine, fibrous; white, close to NN155D, in color.

*Rooting habit*.—Moderately freely branching; medium density.

Plant description:

*Plant and growth habit*.—Perennial shrub; compact, semi-upright to outwardly arching and rounded plant habit; moderately vigorous growth habit; and moderate to fast growth rate.

*Plant height*.—About 20 cm.

*Plant diameter*.—About 35 cm.

*Lateral branch description*.—Branching habit: Freely branching habit; pinching enhances lateral branch development; about 15 to 20 lateral branched develop per plant giving a dense and bushy appearance. Length: About 30 cm to 40 cm. Diameter: About 1 mm to 5 mm. Internode length: About 8 mm. Texture: Smooth, glabrous. Color: Close to N199 and 192C.

Phyllode description:

*Arrangement*.—Phyllodes alternate, simple.

*Length*.—About 5.5 cm.

*Width*.—About 2.6 cm.

*Shape*.—Lanceolate, falcate.

*Apex*.—Slightly acuminate.

*Margin*.—Entire.

*Texture, upper and lower surfaces*.—Smooth, glabrous; slightly viscid.

*Venation pattern*.—Pinnate, arcuate.

*Color*.—Developing phyllodes, upper and lower surfaces: Close to 144A. Fully expanded phyllodes, upper and lower surfaces: Close to N137A venation, close to N137A.

Flower description: Flower development has not been observed on plants of the new *Acacia*.

Disease & pest tolerance: Plants of the new *Acacia* have not been noted to be resistant to pathogens and pests common to *Acacia* plants.

Garden performance: Plants of the new *Acacia* have been observed to have good garden performance and to tolerate rain, wind, full sunlight and temperatures from about −2° C. to about 45° C.

It is claimed:

1. A new and distinct *Acacia* plant named 'ACCOG01' as illustrated and described.

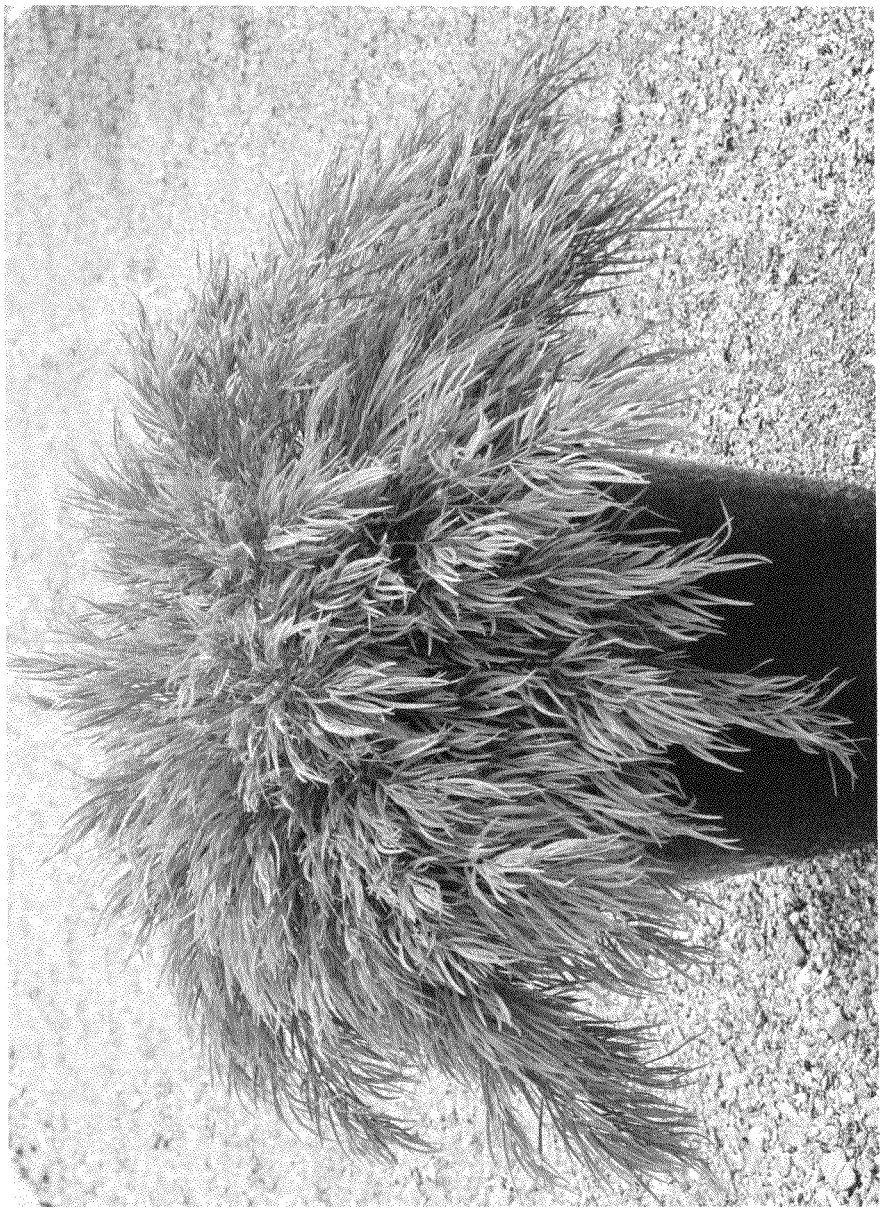

* * * * *